United States Patent
Ito et al.

(10) Patent No.: US 9,151,669 B2
(45) Date of Patent: Oct. 6, 2015

(54) INSPECTING DEVICE AND INSPECTING METHOD

(71) Applicants: DAINIPPON SCREEN MFG. CO., LTD., Kyoto-Shi, Kyoto (JP); OSAKA UNIVERSITY, Suita-shi, Osaka (JP)

(72) Inventors: Akira Ito, Kyoto (JP); Hidetoshi Nakanishi, Kyoto (JP); Masayoshi Tonouchi, Suita (JP); Iwao Kawayama, Suita (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 0 days.

(21) Appl. No.: 14/192,611

(22) Filed: Feb. 27, 2014

(65) Prior Publication Data

US 2014/0239182 A1    Aug. 28, 2014

(30) Foreign Application Priority Data

Feb. 28, 2013  (JP) ................. 2013-039702

(51) Int. Cl.

| | |
|---|---|
| *G01J 1/42* | (2006.01) |
| *G01N 21/63* | (2006.01) |
| *G01R 31/311* | (2006.01) |
| *G01N 21/95* | (2006.01) |
| *G01N 21/956* | (2006.01) |

(52) U.S. Cl.
CPC . *G01J 1/42* (2013.01); *G01N 21/63* (2013.01); *G01N 21/9501* (2013.01); *G01N 21/956* (2013.01); *G01R 31/311* (2013.01)

(58) Field of Classification Search
CPC .......... G01N 21/3581; G01N 21/9501; G01N 21/9505; G01N 21/956; G01J 1/42
USPC ......................................... 250/351
See application file for complete search history.

(56) References Cited

U.S. PATENT DOCUMENTS

| | | | |
|---|---|---|---|
| 8,129,683 B2 | 3/2012 | Itsuji et al. | |
| 2001/0029436 A1* | 10/2001 | Fukasawa | ................. 702/117 |
| 2011/0216312 A1 | 9/2011 | Matsumoto et al. | |

FOREIGN PATENT DOCUMENTS

| | | |
|---|---|---|
| EP | 1441233 A1 | 7/2004 |
| EP | 2 607 945 A2 | 6/2013 |
| JP | 2009-175127 A | 8/2009 |

(Continued)

OTHER PUBLICATIONS

H. Murakami et al., "Laser terahertz emission microscopy," Comptes Rendus Physique, Elsevier, Paris Fr., Science Direct, C. R. Physique 9 (2008) 169-183, Institute of Laser Engineering.

(Continued)

*Primary Examiner* — Marcus Taningco
(74) *Attorney, Agent, or Firm* — McDermott Will & Emery LLP (57) ABSTRACT

An inspecting device inspects an inspecting target that is a semiconductor device or a photo device. The inspecting device includes: a stage for holding an inspecting target; a femtosecond laser for emitting pulsed light; a galvano mirror for obliquely irradiating the inspecting target with the pulsed light, while changing an optical path of the pulsed light, to scan the inspecting target with the pulsed light; and a detection part for detecting an electromagnetic wave emitted non-coaxially with the pulsed light from the inspecting target in accordance with the illumination with the pulsed light.

5 Claims, 9 Drawing Sheets

(56) References Cited

FOREIGN PATENT DOCUMENTS

| | | |
|---|---|---|
| JP | 2010-60317 | 3/2010 |
| JP | 2013-19861 | 1/2013 |

OTHER PUBLICATIONS

Extended European Search Report issued in European Application No. 14153847.0-1504 dated Jun. 26, 2014.

* cited by examiner

INSPECTING DEVICE AND INSPECTING METHOD

BACKGROUND OF THE INVENTION

1. Field of the Invention

The present invention relates to a technique for inspecting a semiconductor device or a photo device.

2. Description of the Background Art

There is already known a semiconductor inspecting device which detects an electromagnetic wave emitted from a semiconductor device by irradiating it with pulsed laser light, thereby to inspect the semiconductor device in non-contact (e.g., Japanese Patent Application Laid-Open No. 2010-60317). In the semiconductor inspecting device described in Japanese Patent Application Laid-Open No. 2010-60317, a previously set inspection range is scanned with pulsed laser light in the semiconductor device by use of a galvanometer scanner. Then, the generated electromagnetic wave (terahertz wave) is detected, thereby to image its intensity distribution.

Further, the present applicant proposed a technique of irradiating a photo device with pulsed light and detecting an electromagnetic wave emitted from the photo device accordingly, thereby to inspect the photo device (Japanese Patent Application Laid-Open No. 2013-19861). In Japanese Patent Application Laid-Open No. 2013-19861. it is proposed that the photo device is moved in two-dimensional directions, thereby to scan the photo device with pulsed light.

As in the semiconductor inspecting device described in Japanese Patent Application Laid-Open No. 2010-60317, scanning by means of the galvano scanner enables relatively high-speed inspection of a certain range of an inspecting target. However, the semiconductor inspecting device described in Japanese Patent Application Laid-Open No. 2010-60317 is a so-called coaxial epi-illumination type inspecting device where the pulsed laser light, with which the semiconductor device is irradiated, is coaxial with the detected terahertz wave. In such a coaxial epi-illumination type inspecting device, it has been necessary to provide an optical plate with an ITO film so as to reflect the terahertz wave while transmitting the pulsed laser light. This might lead to a complicated configuration of the inspecting device, and improvement has thus been required.

SUMMARY OF THE INVENTION

The present invention is directed to an inspecting device for taking a semiconductor device or a photo device as an inspecting target.

An inspecting device according to a first aspect includes: a light source for emitting pulsed light; a scan part for obliquely irradiating an inspecting target with the pulsed light, while changing an optical path of the pulsed light, to scan the inspecting target with the pulsed light; and a detection part for detecting an electromagnetic wave emitted non-coaxially with the pulsed light from the inspecting target in accordance with the illumination with the pulsed light.

According to the inspecting device in the first aspect, it is possible to perform high speed scanning with pulsed light by means of a scanning mechanism. Further, since an electromagnetic wave emitted in a cross direction is detected, it is not necessary to use the optical plate with an ITO film for reflecting the electromagnetic wave, emitted coaxially with the pulsed light, in another direction as hitherto been. Hence it is possible to simplify the device configuration.

An inspecting device according to a second aspect is the inspecting device according to the first aspect, wherein the detection part is provided with a detector for receiving pulsed light emitted from the light source as probe light, to detect the electromagnetic wave, and the inspecting device further includes a delay part for delaying the arrival timing of the probe light at the detector relatively to the arrival timing of the electromagnetic wave.

According to the inspecting device in the second aspect, it is possible to restore a temporal waveform of the electromagnetic wave.

An inspecting device according to a third aspect is the inspecting device according to the first or second aspect, further including an image generation part for generating an image indicating electric field intensity distribution of the inspecting target based on an electric field intensity of an electromagnetic wave detected by the detection part.

According to the inspecting device in the third aspect, it is possible to visually grasp electric field intensity distribution.

An inspecting device according to a fourth aspect is the inspecting device according to the third aspect, wherein the image generation part decides a position on the image which corresponds to an acquisition point of an electromagnetic wave intensity based on an incidence angle of the pulsed light on the inspecting target.

Further, the present invention is directed to an inspecting method for taking a semiconductor device or a photo device as an inspecting target.

An inspecting method according to a fifth aspect includes the steps of: (a) emitting pulsed light from a light source; (b) obliquely irradiating an inspecting target with the pulsed light emitted in the step (a), while changing an optical path of the pulsed light, to scan the inspecting target with the pulsed light; and (c) detecting an electromagnetic wave emitted non-coaxially with the pulsed light from the inspecting target in accordance with the illumination with the pulsed light in the step (b).

Accordingly, it is an object of the present invention to provide a technique for simplifying a device configuration for scanning an inspecting target with pulsed light.

These and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, a preferred embodiment of the present invention will be described with reference to the accompanying drawings. In the drawings, dimensions or the number of respective parts may be shown as being exaggerated or simplified according to the need in order to facilitate understanding. Further, constitutional elements described in this preferred embodiment are thoroughly examples, and not aimed at restricting the scope of the present invention thereto.

Figure 1:
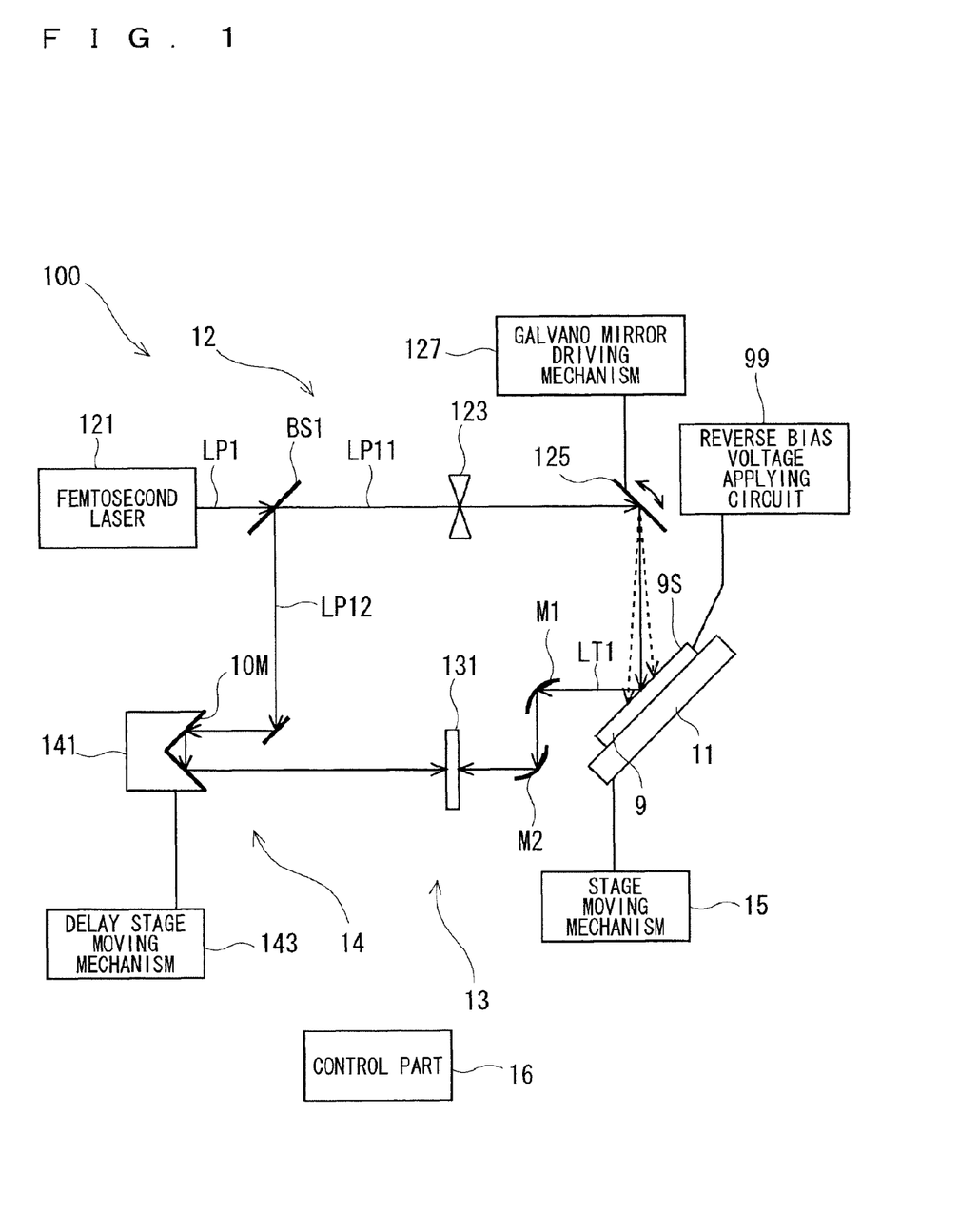
FIG. 1 is a schematic constitutional diagram of an inspecting device according to a preferred embodiment.

FIG. 1 is a schematic constitutional diagram of an inspecting device 100 according to a preferred embodiment. The inspecting device 100 irradiates an inspecting target 9 being a semiconductor device or a photo device with pulsed light, and detects an electromagnetic wave (e.g., terahertz wave with a frequency of 0.1 to 30 THz) emitted from the inspecting target 9 in accordance with the irradiation with the pulsed light, to inspect the inspecting target 9.

In the present application, the semiconductor device is an electronic device configured of a semiconductor, such as a transistor, an integrated circuit (IC or LSI), a resistor or a capacitor. Further, the photo device is an electronic device that utilizes a photoelectric effect of a semiconductor, such as a photodiode, an image sensor like a CMOS sensor or a CCD sensor, a solar cell, an LED or the like. Although it is assumed that a surface 9S of the inspecting target 9 is formed in a planar shape, it may be formed in a curved shape or the like.

As shown in FIG. 1, the inspecting device 100 includes a stage 11, an irradiation part 12, a detection part 13, a delay part 14, a stage moving mechanism 15, and a control part 16.

The inspecting target 9 is fixed onto the stage 11 by fixing means, not shown, and held thereon. Examples of the fixing means may include means utilizing an interposing tool for interposing the inspecting target 9, an adhesive sheet, and an adsorption hole formed on the surface of the stage 11. However, fixing means other than these may be adopted so long as it can hold the inspecting target 9.

The irradiation part 12 is provided with a femtosecond laser 121 as a light source for emitting pulsed light. The femtosecond laser 121 emits pulsed light (pulsed light LP1) with a wavelength that includes a visible light region of not smaller than 360 nm (nanometers) and not larger than 1.5 µm (micrometer), for example. As a specific example, pulsed light to be linearly polarized light having a center wavelength in the vicinity of 800 nm, a cycle of several kHz to several hundred MHz, and a pulse width of approximately 10 to 150 femtoseconds is emitted from the femtosecond laser. As a matter of course, pulsed light with another wavelength range (visible light wavelength such as a blue wavelength (450 to 495 nm) or a green wavelength (495 to 570 nm)) may be emitted.

The pulsed light LP1 emitted from the femtosecond laser 121 is divided into two portions by means of a beam splitter BS1. The one divided pulsed light (pulsed light LP11) is guided to the inspecting target 9. Further, the other pulsed light (probe light LP12) is guided to a detector 131 of the detection part 13 for detecting an electromagnetic wave.

The pulsed light LP11 is modulated by an optical chopper 123 at several kHz. It is to be noted that as the modulation element, an AOM (Acousto-Optic Modulator) or the like may be used. The pulsed light LP11 modulated by the optical chopper 123 is reflected by a galvano mirror 125 and guided to the inspecting target 9.

The galvano mirror 125 changes an optical path of the pulsed light LP11, thereby to scan the inside of an inspecting target range, set in the inspecting target 9, with the pulsed light LP11. The galvano mirror 125 is driven by a galvano mirror driving mechanism 127. The inspecting target 9 is irradiated with the pulsed light LP11 by the galvano mirror 125 while being scanned thereby in two directions vertical to an optical axis of the pulsed light LP11. The galvano mirror 125 and the galvano mirror driving mechanism 127 are examples of the scanning mechanism. It is to be noted that other than the galvano mirror 125, a polygon mirror, a piezo mirror, an acousto-optic device or the like can be used.

When a portion in the inspecting target 9 where an internal electric field exists is irradiated with the pulsed light LP11 having energy beyond a band gap, a free electron and a free hole are generated and accelerated by the internal electric field. A pulsed-current is thereby generated, and accordingly, an electromagnetic wave is generated. The internal electric field is known to be generated in a pn junction part, a Schottky barrier junction part or the like, for example.

An electromagnetic wave LT1 is generated depending on the state (intensity, direction, etc.) of the internal electric field. That is, the electromagnetic wave LT1 is generated depending on a pn bond, a state of wiring connected to the pn bond, and the like. Therefore, detecting the electromagnetic wave LT1 allows investigation of characteristics of the inspecting target 9 and inspection such as defect judgment.

The electromagnetic wave LT1 emitted from the inspecting target 9 is collected in parabolic mirrors M1, M2. More specifically, the parabolic mirrors M1, M2 collect the electromagnetic wave LT1 emitted on the same side as the surface 9S that is irradiated with the pulsed light LP11. Then, the collected electromagnetic wave LT1 is incident on the detector 131.

The detector 131 is configured of a photoconductive switch, on which the probe light LP12 is incident. When the detector 131 is irradiated with the probe light LP12 in a state where the electromagnetic wave LT1 is incident on the detector 131, a current in accordance with an electric field intensity of the electromagnetic wave LT1 is instantaneously generated in the photoconductive switch. The current corresponding to the electric field intensity is converted into a digital quantity through an I/V conversion circuit, an A/D conversion circuit or the like. As thus described, the detection part 13 detects the electric field intensity of the electromagnetic wave LT1 emitted from the inspecting target 9 in accordance with the irradiation with the probe light LP12. It is to be noted that applying another element, such as a Schottky barrier diode or nonlinear optical crystal, to the detector 131 can also be considered.

In the present preferred embodiment, the planar surface 9S of the planar inspecting target 9 is obliquely irradiated with the pulsed light LP11, and the electromagnetic wave LT1 emitted non-coaxially with the pulsed light LP11 is collected in parabolic mirrors M1, M2, and then detected by the detector 131. It is to be noted that "obliquely irradiated" means an optical axis of the pulsed light LP11 is not orthogonal to the surface 9S. When the surface 9S is not planar, there is assumed a plane which is located at a point of intersection of the surface 9S and the pulsed light LP11, and is in contact with the surface 9S. Then the plane and the optical axis of the pulsed light LP11 are set so as not to orthogonal to each other, whereby the surface 9S is obliquely irradiated with the pulsed light LP11.

The semiconductor inspecting device described in Japanese Patent Application Laid-Open No. 2010-60317 is an epi-illumination type inspecting device for detecting an electromagnetic wave emitted coaxially with the pulsed laser, with which irradiation is performed. For this reason, the optical plate with an ITO film which transmits the pulsed light LP11 and reflects the electromagnetic wave (mainly terahertz wave) is essential, and there is a restriction that the optical plate should be arranged on the optical paths of the pulsed light LP11 and the terahertz wave. As opposed to this, since the inspecting device 100 according to the present preferred embodiment is a so-called reflection type inspecting device, it does not need the optical plate with an ITO film, and its configuration can thus be simplified.

The delay part 14 is provided on an optical path of the probe light LP12 from the beam splitter BS1 to the detector 131. The delay part 14 is an optical element for continuously changing the arrival time of the probe light LP12 at the detector 131. The delay part 14 is provided with a delay stage 141 and a delay stage moving mechanism 143. The delay stage 141 is provided with a return minor 10M for returning the probe light LP12 in an incident direction. Further, the delay stage moving mechanism 143 moves the delay stage 141 parallelly along the incident direction of the probe light LP12 based on control of the control part 16. The parallel movement of the delay stage 141 leads to a continuous change in optical path length of the probe light LP12 from the beam splitter BS1 to the detector 131.

The delay stage 141 changes the time difference between the arrival time of the electromagnetic wave LT1 at the detector 131 and the arrival time of the probe light LP12 at the detector 131. In other words, changing the optical path length of the probe light LP12 by the delay stage 141 delays the timing (detection timing or sampling timing) for detecting the electric field intensity of the electromagnetic wave LT1 in the detector 131.

It is to be noted that the arrival time of the probe light LP12 at the detector 131 can be changed by another configuration different from that of the delay stage 141. Specifically, utilizing an electro-optical effect is considered. In other words, an electro-optic element having a refractive index which changes by changing an applied voltage may be used as a delay element. For example, an electro-optic element disclosed in Japanese Patent Application Laid-Open No. 2009-175127 can be utilized.

Furthermore, it is also possible to change an optical path length of the pulsed light LP11 (pump light) or an optical path length of the electromagnetic wave LT1 emitted from the inspecting target 9. Also in this case, the arrival time of the electromagnetic wave LT1 at the detector 131 can be relatively shifted from the arrival time of the probe light LP12 at the detector 131. That is, it is possible to delay the detection timing for the electric field intensity of the electromagnetic wave LT1 in the detector 131.

Further, the inspecting device 100 includes a reverse bias voltage applying circuit 99 for applying a reverse bias voltage to the inspecting target 9 at the time of inspection. When the inspecting target 9 is a solar cell, for example, the reverse bias voltage applying circuit 99 is connected to electrodes respectively formed on the light receiving surface of the solar cell and the opposite-side surface thereto, and a reverse bias voltage is applied. Applying the reverse bias voltage can increase a depletion layer of the pn junction part. Hence it is possible to increase the electric field intensity of the electromagnetic wave LT1 detected in the detector 131, so as to improve detection sensitivity of the electromagnetic wave LT1 in the detection part 13. However, it is also possible to omit the reverse bias voltage applying circuit 99.

The stage moving mechanism 15 is a device for moving the stage 11 in a two-dimensional plane and is configured of an X-Y table or the like, for example. The stage moving mechanism 15 moves the inspecting target 9 held on the stage 11 relatively to the irradiation part 12. The inspecting device 100 can move the inspecting target 9 to an arbitrary position in the two-dimensional plane by means of the stage moving mechanism 15.

Figure 2:
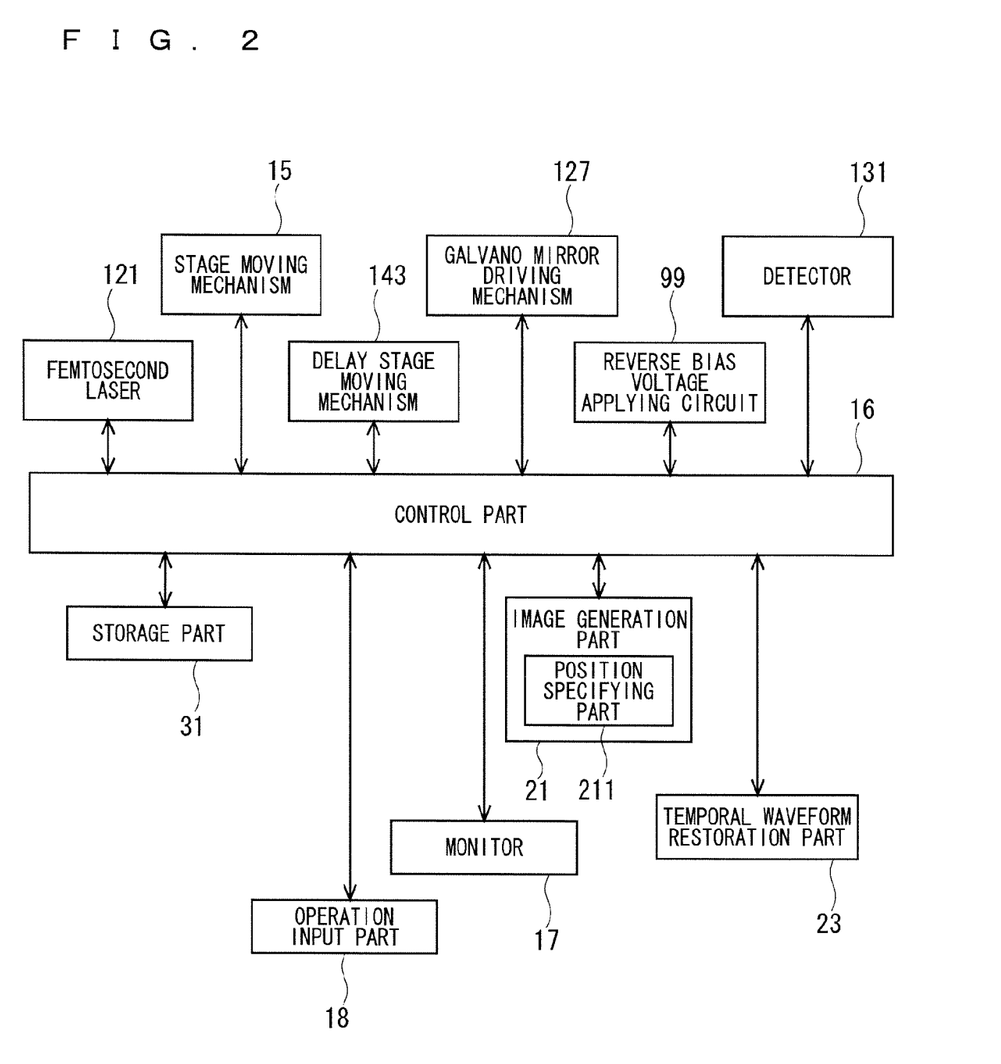
FIG. 2 is a block diagram showing connection between a control part and other elements.

FIG. 2 is a block diagram showing connection between the control part 16 and other elements. The control part 16 is configured of a general computer or the like, provided with a CPU, a ROM, a RAM and the like which are not shown. As shown in FIG. 2, the control part 16 is connected to the femtosecond laser 121, the detector 131 the delay stage moving mechanism 143, the stage moving mechanism 15, the galvano mirror driving mechanism 127 and the reverse bias voltage applying circuit 99. The control part 16 controls an operation of each of these elements or receives data from each of these elements.

Further, the control part 16 is connected to an image generation part 21 and a temporal waveform restoration part 23. The image generation part 21 and the temporal waveform restoration part 23 are functions realized by the CPU provided in the control part 16, but those may be realized on a hardware basis by means of a dedicated circuit.

In the inspection target range of the inspecting target 9 (part or the whole of the inspecting target 9), the image generation part 21 generates an electric field intensity distribution image formed by visualizing distribution of the electric field intensity of the electromagnetic wave LT1 emitted by the irradiation with the pulsed light LP11. In the electric field intensity distribution image, a difference in electric field intensity is visually expressed by different colors, different patterns or the like, for example.

The image generation part 21 is provided with a position specifying part 211. The position specifying part 211 specifies a position corresponding to an acquisition point of electromagnetic wave intensity data on an electric field intensity distribution image based on an incidence angle of pulsed light. A specific process contents to be executed by the position specifying part 211 will be detailed later.

The temporal waveform restoration part 23 restores a temporal waveform of the electromagnetic wave LT1 emitted from the inspecting target 9 based on an electric field intensity detected in the detector 131. Specifically, by moving the delay stage 141, the arrival time of the probe light LP12 at the detector 131 is changed, to acquire the electric field intensity of the electromagnetic wave LT1 detected in each phase. Then, the acquired electric field intensity is plotted on a temporal axis, to restore the temporal waveform of the electromagnetic wave LT1.

The control part 16 is connected with a storage part 31 for storing a variety of data. The storage part 31 may be configured of a portable media (e.g., magnetic media, optical disk media, semiconductor memory, etc.) or the like other than a fixed disk such as a hard disk. Further, the control part 16 may be connected with the storage part 31 through a network line.

The control part 16 is connected with a monitor 17 and an operation input part 18. The monitor 17 is a display device such as a liquid crystal display, and displays a variety of image information to an operator. The monitor 17 displays an image of the surface 9S of the inspecting target 9, photographed by a visible camera or the like, the electric field intensity distribution image generated by the image generation part 21, the temporal waveform of the electromagnetic wave LT1 restored by the temporal waveform restoration part 23, and the like. Further, the monitor 17 displays a GUI (Graphical User Interface) screen which is necessary for setting inspection conditions (inspection range, rotating angle of the galvano mirror 125, etc.).

The operation input part 18 is configured of a variety of input devices such as a mouse and a keyboard. The operator can perform a predetermined operation input through the operation input part 18. It is to be noted that the monitor 17 may be configured as a touch panel, thereby to function as the operation input part 18.

<About Occurrence of Optical Path Difference>

Figure 3:
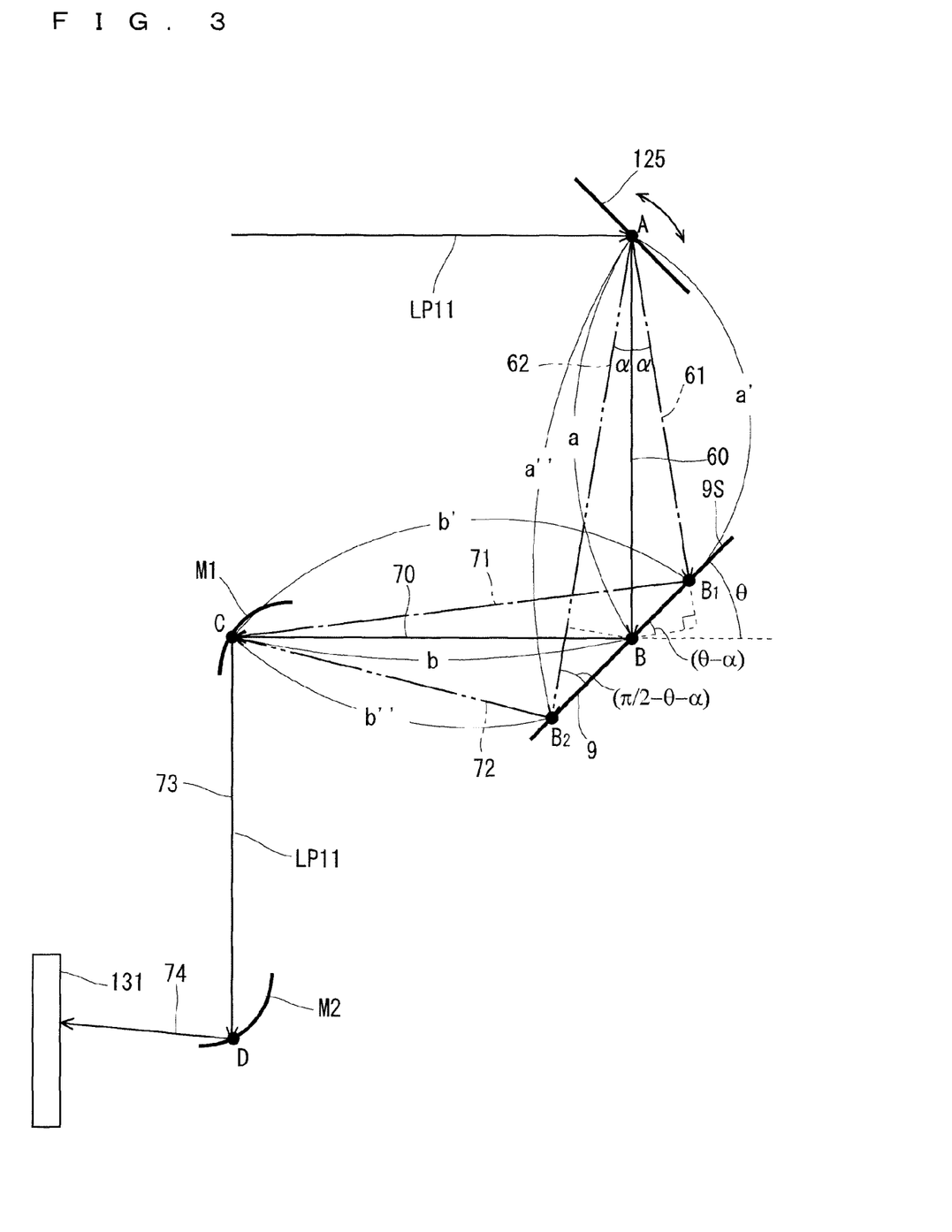
FIG. 3 is a diagram for explaining an optical path difference of pulsed light which occurs at the time of scanning.

When the optical path of the pulsed light LP11 is changed by the galvano mirror 125, an optical path difference occurs in the case of irradiating a front-side position and a back-side position. However, the occurrence of this optical path difference can be ignored in terms of measurement, and a detailed description will be made on this regard.

FIG. 3 is a diagram for explaining an optical path difference of the pulsed light LP11 which occurs at the time of scanning. It is to be noted that an electromagnetic wave LT1 generated from the inspecting target 9 is reflected twice each on the parabolic mirrors M1, M2. However, FIG. 3 shows an approximated state where an electromagnetic wave LT1 is reflected just once each on the parabolic mirrors M1, M2 in order to facilitate the explanation.

In the example shown in FIG. 3, by driving the galvano mirror 125, the optical path of the pulsed light LP11 is changed to the right and left with a predetermined optical path 60 at the center. Specifically, the predetermined optical path 60 is a path of the pulsed light LP11 connecting a point A (position on which the pulsed light LP11 modulated by the optical chopper 123 is incident) on the galvano mirror 125 to a point B on the inspecting target 9. The optical path 61 is one formed by clockwise rotating the predetermined optical path 60 around the point A by an angle α. The optical path 62 is one formed by counter-clockwise rotating the predetermined optical path 60 around the point A by the angle α. The optical path 61 and the optical path 62 respectively extend from the point A to a point $B_1$ and a point $B_2$ on the inspecting target 9.

In the following description, an incidence angle of the pulsed light LP11, which travels on the predetermined optical path 60, on the surface 9S of the inspecting target 9 is set to be "θ". That is, in the example shown in FIG. 3, a platy inspecting target 9 is inclined by the angle θ with respect to an orthogonal direction to the optical path 60.

Further, in the following description, an optical path length of the optical path 60 is set as "a", an optical path length of the optical path 61 is set as "a'", and an optical path length of the optical path 62 is set as "a''".

An optical path 70 indicates a path of the electromagnetic wave LT1 emitted from the point B, which is a path connecting the point B to a point C of the parabolic mirror M1. Further, an optical path 71 indicates a path of the electromagnetic wave LT1 emitted from the point $B_1$, which is a path connecting the point $B_1$ to the point C. Moreover, an optical path 72 indicates a path of the electromagnetic wave emitted from the point $B_2$, which is a path connecting the point $B_2$ to the point C. In the following description, an optical path length of the optical path 70 is set as "b", an optical path length of the optical path 71 is set as "b'", and an optical path length of the optical path 72 is set as "b''".

As apparent from FIG. 3, the optical path length of the optical path 61 is shorter than that of the predetermined optical path 60 (a'<a), but the optical path length of the optical path 71 of the electromagnetic wave LT1 emitted by the pulsed light LP11 of the optical path 61 is longer than that of the predetermined optical path 70 (b'>b). Meanwhile, the optical path length of the optical path 62 is longer than that of the predetermined optical path 60 (a''>a), but the optical path length of the optical path 72 of the electromagnetic wave LT1 emitted by the pulsed light LP11 of the optical path 62 is shorter than that of the predetermined optical path 70 (b''<b). That is, when a difference between a sum of the optical path lengths of the optical path 61 and the optical path 71 and a sum of the optical path lengths of the optical path 62 and the optical path 72 is calculated, it is found to be in an ignorable range. A detailed review will be made on this regard.

Figure 4:
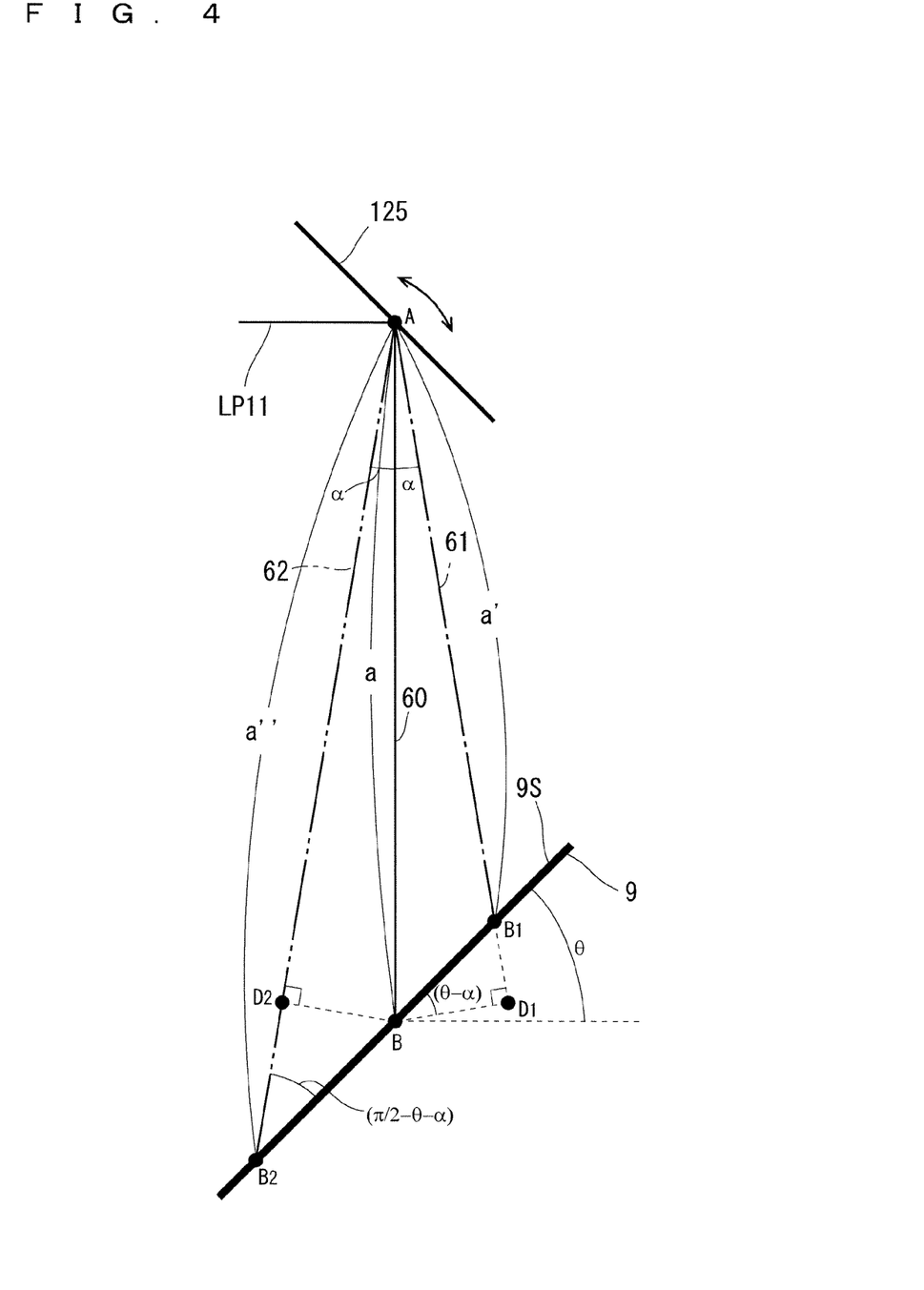
FIG. 4 is a diagram showing an optical path of pulsed light from a galvano mirror to an inspecting target.

First, the optical path lengths, a, a', a'' will be reviewed. FIG. 4 is a diagram showing the optical path of the pulsed light LP11 from the galvano mirror 125 to the inspecting target 9.

First, an intersection point at the time of extending a line segment (line segment $AB_1$) of the optical path 61 and extending a vertical line from the point B to the extended line is set as $D_1$. Then, the optical path length a' of the optical path 61 is expressed by the following equation:

$$a' = AD_1 - B_1D_1 \quad \text{(Equation 1)}$$
$$= a \cdot \cos\alpha - BD_1 \cdot \tan(\theta - \alpha)$$
$$= a \cdot \cos\alpha - a \cdot \sin\alpha \cdot \tan(\theta - \alpha)$$

Further, an intersection point at the time of extending a vertical line from the point B to a line segment (line segment $AB_2$) of the optical path 62 is set as a point $D_2$. Then, the optical path length a'' of the optical path 62 is expressed by the following equation:

$$a'' = AD_2 + B_2D_2 \quad \text{(Equation 2)}$$
$$= a \cdot \cos\alpha + BD_2 / \tan(\pi/2 - \theta - \alpha)$$
$$= a \cdot \cos\alpha + a \cdot \sin\alpha \cdot \tan(\pi/2 - \theta - \alpha)$$

Figure 5:
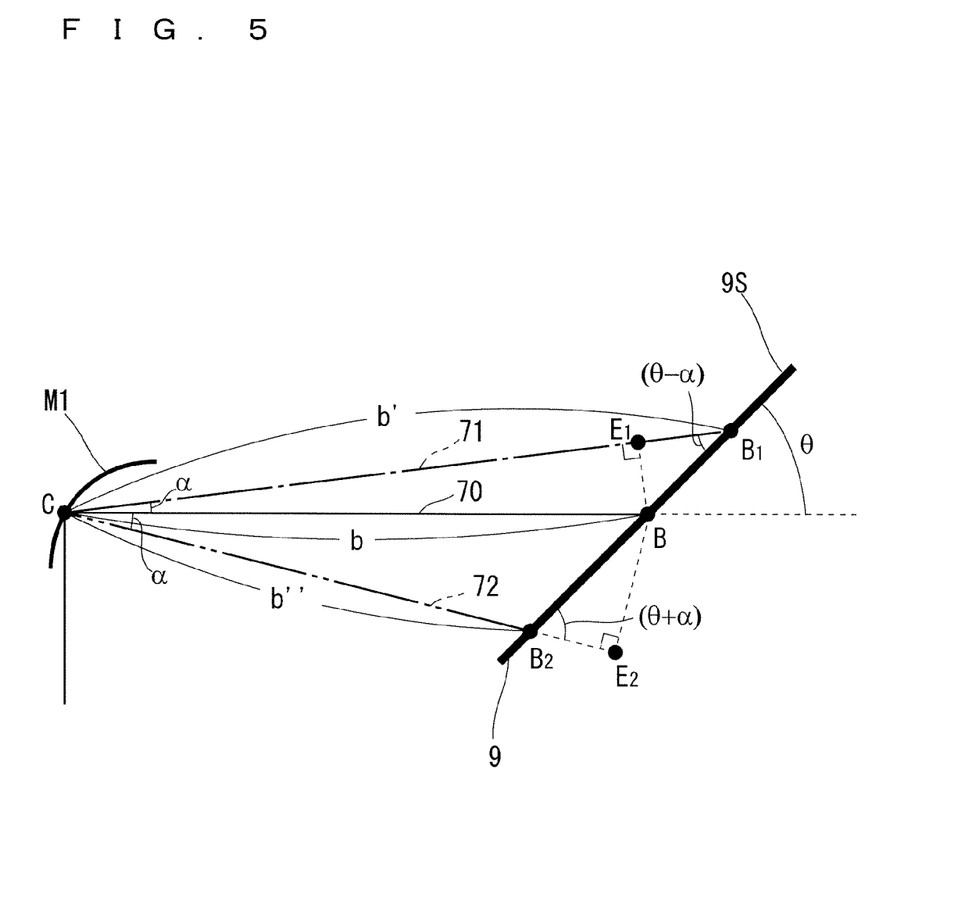
FIG. 5 is a diagram showing an optical path of an electromagnetic wave from the inspecting target to a parabolic mirror.

Next, the optical path lengths, b, b', b'' will be reviewed with reference to FIG. 5. FIG. 5 is a diagram showing the optical path of the electromagnetic wave LT1 from the inspecting target 9 to the parabolic mirror M1.

An intersection point at the time of extending a vertical line from the point B to a line segment (line segment $B_1C$) of the optical path 71 is set as a point $E_1$. Then, the optical path length b' of the optical path 71 is expressed by the following equation:

$$b' = CE_1 + E_1B_1 \quad \text{(Equation 3)}$$
$$= b \cdot \cos\alpha + E_1B / \tan(\theta - \alpha)$$
$$= b \cdot \cos\alpha + b \cdot \sin\alpha / \tan(\theta - \alpha)$$

Further, an intersection point at the time of extending a line segment of the optical path 72 and extending a vertical line from the point B to the extended line is set as $E_2$. Then, the optical path length b'' of the optical path 72 is expressed by the following equation:

$$b'' = CE_2 - E_2B_2 \quad \text{(Equation 4)}$$
$$= b \cdot \cos\alpha + E_2B / \tan(\theta + \alpha)$$
$$= b \cdot \cos\alpha - b \cdot \sin\alpha / \tan(\theta + \alpha)$$

A total of the optical path length a' and the optical path length b' is expressed by the following equation using the optical path lengths a, b:

$$a'+b'=(a+b)\cos\alpha\cdot\sin\alpha\cdot\tan(\theta-\alpha)+b\cdot\sin\alpha/\tan(\theta-\alpha) \quad \text{(Equation 5)}$$

Further, a total of the optical path length a″ of the optical path 62 and the optical path length b″ of the optical path 72 is expressed by the following equation using the optical path lengths a, b:

$$a''+b''=(a+b)\cos\alpha+a\cdot\sin\alpha/\tan(\pi/2-\theta-\alpha)-b\cdot\sin\alpha/\tan(\theta+\alpha)$$ (Equation 6)

When these values are substituted into Equations 5 and 6 where the optical path length a=b=0.1 (m), α=2.862° and θ=45°, a'+b' is 0.20075 (m), and a″+b″ is 0.20075 (m). That is, in the range of five significant figures, a'+b'=a″+b″, and an optical path difference can be ignored.

It is to be noted that changing the optical path length of the pulsed light LP11 also leads to occurrence of an optical path difference between the optical path length of the electromagnetic wave LT1 from the parabolic mirror M1 to the parabolic mirror M2 and the optical path length of the electromagnetic wave LT1 from the parabolic mirror M2 to the detector 131. However, the electromagnetic wave LT1 is a terahertz wave with a wavelength of several hundred μm to several mm. The optical path difference that occurs from the parabolic mirror M1 to the detector 131 is shorter than the wavelength of the terahertz wave, and it can thus be ignored.

<Inspection>

Figure 6:
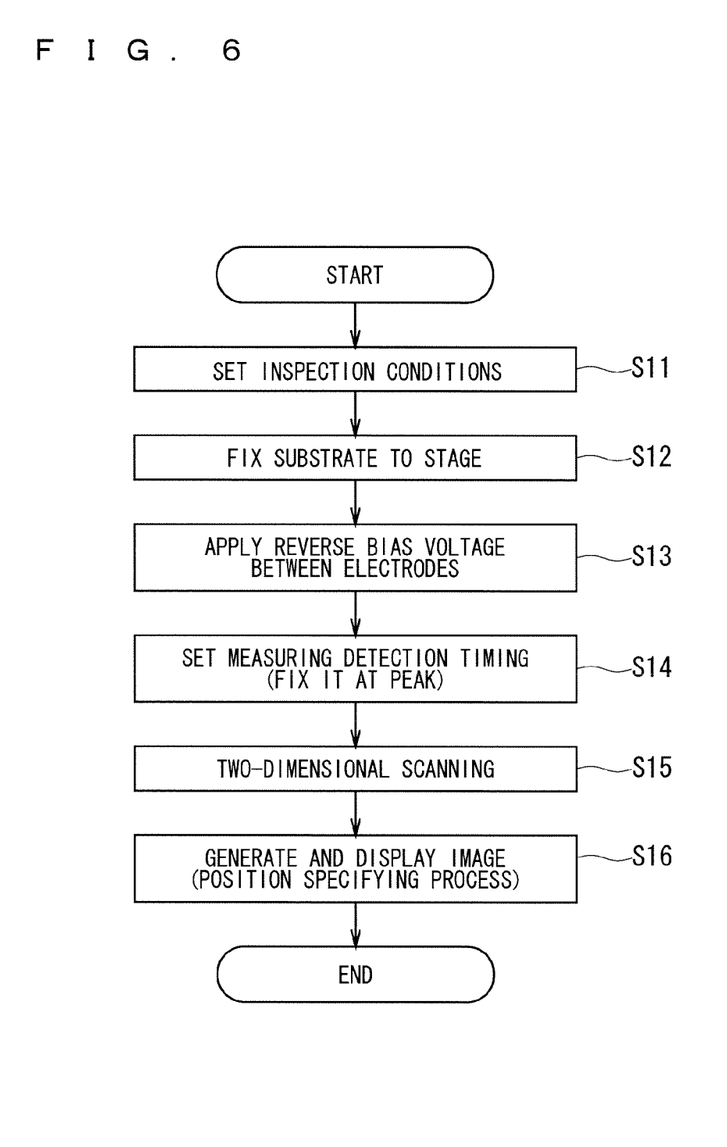
FIG. 6 is a flowchart showing an example of an inspection for the inspecting target.

FIG. 6 is a flowchart showing an example of an inspection for the inspecting target 9. In the following description, it is assumed that each operation of the inspecting device 100 is controlled by the control part 16 unless otherwise mentioned. Further, depending on the contents of steps, a plurality of steps may be executed in parallel or the order for executing each step may be changed as appropriate.

First, inspection conditions are set in the inspecting device 100 (FIG. 6: step S11). Specifically, an inspection range, a scanning speed (rotational speed of the galvano mirror 125) and the like are set.

Next, the inspecting target 9 to be an inspection target is fixed to the stage 11 (FIG. 6: step S12). In this step S12, the inspecting target 9 may be delivered to the stage 11 by the operator or the inspecting target 9 may be delivered to the stage 11 by a delivery device or the like which is not shown. It is to be noted that, when the inspecting target 9 is a photo device (solar cell, photosensor, etc.) for outputting a current by receiving light, the inspecting target 9 is provided such that the light receiving surface is irradiated with the pulsed light LP11. Further, after installation of the inspecting target 9 on the stage 11, the stage 11 may be moved, thereby to move the inspecting target 9 to a required position such that a previously set inspection region can be irradiated with the pulsed light LP11.

When the inspecting target 9 is a photo device such as a solar cell or a photosensor, the surface 9S is desirably the light receiving surface. This is because the light receiving surface of the solar cell or the photosensor is typically made up so as to be easy to absorb light, and irradiating the light receiving surface with the pulsed light LP11 can thus bring about favorable generation of the electromagnetic wave.

When the inspecting target 9 is provided on the stage 11, the reverse bias voltage applying circuit 99 is connected to the inspecting target 9, and a reverse bias voltage is applied (FIG. 6: step S13). It is to be noted that this step S13 can be omitted. For example, when the inspecting target 9 is the solar cell, the reverse bias voltage applying circuit 99 is connected respectively to a front electrode (light receiving surface electrode) and a back electrode. Applying the reverse bias voltage can lead to an increase in internal electric field, thereby to allow an increase in intensity of the electromagnetic wave LT1.

Next, the timing for measuring detection by the detection part is set (FIG. 6: step S14). Specifically, by the control part 16 driving the delay stage moving mechanism 143, a position of the return mirror 10M is adjusted such that the arrival timing of the probe light LP12 at the detector 131 is fixed to required measuring detection timing.

In the present preferred embodiment, for example, it is considered that measuring detection timing is fixed in accordance with timing (phase) when the electric field is maximal in a temporal waveform of the electromagnetic wave LT1 emitted from a predetermined position of the inspecting target 9.

Figure 7:
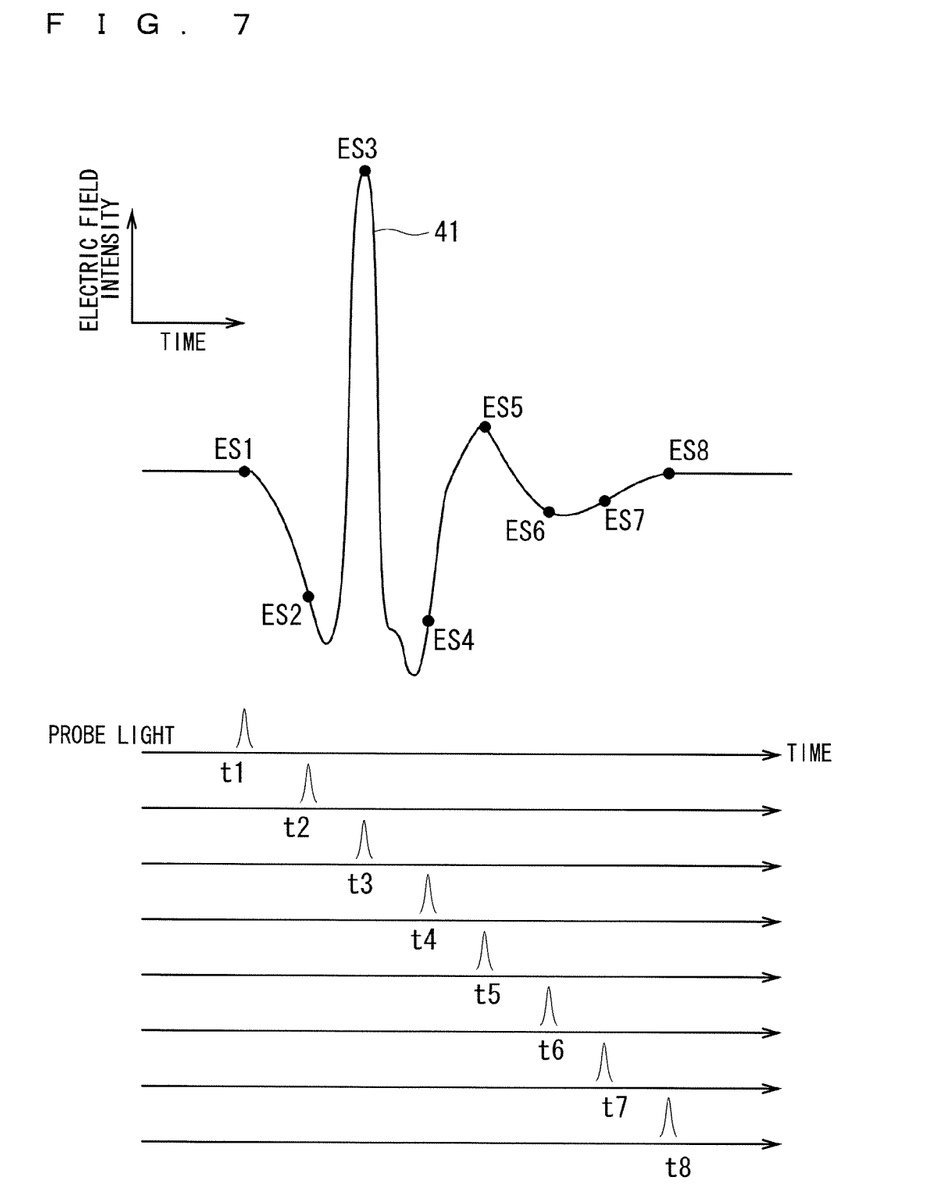
FIG. 7 is a diagram showing a temporal waveform of a restored electromagnetic wave.

FIG. 7 is a diagram showing a temporal waveform 41 of a restored electromagnetic wave LT1. In FIG. 7, a lateral axis indicates the time, and a vertical axis indicates the electric field intensity. Further, on a lower side, there are conceptually shown a plurality of probe light LP12, whose arrival timing at the detector 131 (detection timing t1 to t8) are changed by the delay part 14.

For example, when a specific position where the inspecting target 9 is present is irradiated with the pulsed light LP11, the electromagnetic wave LT1 indicated by the temporal waveform 41 repetitively arrives at the detector 131 in a predetermined cycle. For example, when the delay part 14 is adjusted such that the probe light arrives at the detector 131 at detection timing t1, an electric field intensity having a value ES1 is detected in the detector 131. Further, when the delay part 14 is adjusted to delay the detection timing to t2 to t8, respectively, electric field intensities having values ES2 to ES8 are respectively detected in the detection part 13. In such a manner, the electric field intensity of the electromagnetic wave LT1 is measured while the detection timing is finely changed, and the acquired electric field intensity value is plotted along a temporal axis in a graph, thereby to restore the temporal waveform 41 of the electromagnetic wave LT1.

For example, as shown in FIG. 7, the electric field intensity becomes maximal in the temporal waveform 41 when the detection timing is t3. That is, fixing the delay stage 141 to a position corresponding to the detection timing t3 can lead to detection of the maximum electric field intensity of the electromagnetic wave LT1.

Returning to FIG. 6, when the measuring detection timing is set, the inspecting device 100 drives the galvano mirror 125 to two-dimensionally scan the inspecting target 9 with the pulsed light LP11 (FIG. 6: step S15). At this time, the galvano mirror 125 may be swayed to perform scanning with the pulsed light LP11 in two directions orthogonal to each other, thereby to realize two-dimensional scanning. Alternatively, the galvano mirror 125 may be swayed to perform scanning with the pulsed light LP11 just in one direction (main scanning direction). In this case, for example by combining movement of the stage 11 in a direction (vertical scanning direction) orthogonal to the one direction, the inspecting target 9 can be two-dimensionally scanned with the pulsed light LP11. Further, it can be considered that the whole of the irradiation part 12 is moved in the vertical scanning direction.

When the electric field intensity of the electromagnetic wave LT1 in the inspection range is acquired, the inspecting device 100 generates an image indicating electric field intensity distribution and displays it on the monitor 17 (step S16). In this step, as described above, the position specifying part 211 performs a position specifying process for specifying a position where the electromagnetic wave LT1 has been emitted based on information such as the time of detection of the electromagnetic wave LT1 and an incidence angle of the pulsed light LP11 on the inspecting target 9.

<Position Specifying Process>

Figure 8:
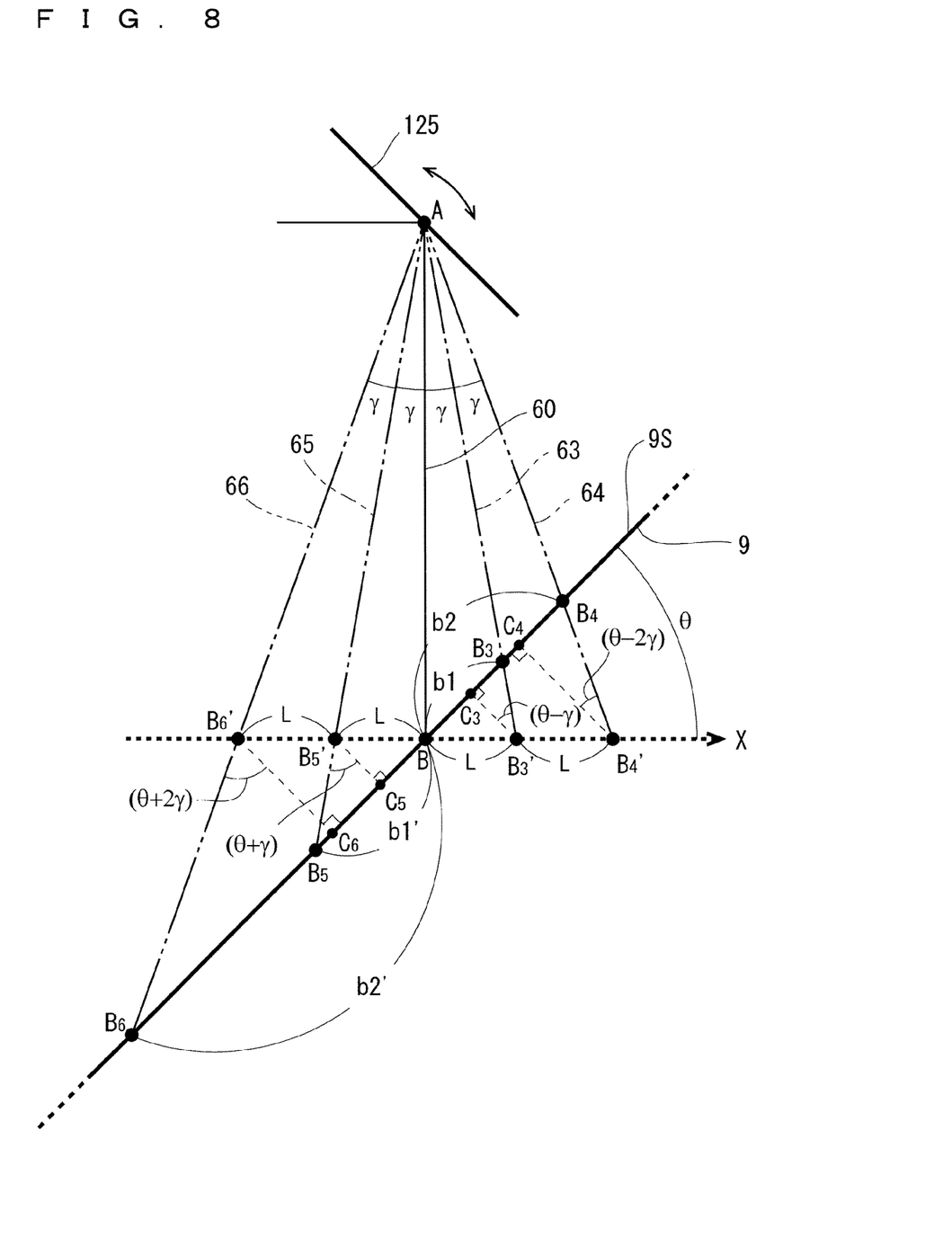
FIG. 8 is a diagram for explaining fluctuations in data acquisition interval which occurs by drive of the galvano mirror.

FIG. 8 is a diagram for explaining fluctuations in data acquisition interval which occurs by drive of the galvano mirror 125. In the present preferred embodiment, it is assumed that data of the electric field intensity of the electromagnetic wave LT1 is acquired every time the galvano mirror 125 is rotated at an angle γ. An optical path 63 and an optical path 64 correspond to ones respectively formed by clockwise rotating the predetermined optical path 60 around the point A by the angle γ and an angle 2γ. The optical path 63 and the optical path 64 are then extended respectively from the point A to a point $B_3$ and a point $B_4$ which are data acquisition points on the inspecting target 9. An optical path 65 and an optical path 66 correspond to ones respectively formed by counter-clockwise rotating the predetermined optical path 60 around the point A by the angle γ and the angle 2γ. The optical path 65 and the optical path 66 are then extended respectively from the point A to a point $B_5$ and a point $B_6$ which are data acquisition points on the inspecting target 9.

A distance between the points B and $B_3$, a distance between the points B and $B_4$, a distance between the points B and $B_5$, and a distance between the points B and $B_6$ are respectively set as "b1", "b2", "b1'" and "b2'". Further, X-axis extending in a direction orthogonal to the predetermined optical path 60 is assumed, and intersection points of the optical paths 63, 64, 65, 66 with the X-axis are respectively set as points $B_3'$, $B_4'$, $B_5'$ and $B_6'$. In order to facilitate understanding, it is assumed that the angle γ is extremely fine, and a length between the points $B_3'$ and $B_4'$, a length between the points $B_3'$ and B, a length between the points B and $B_5'$ and a length between the points $B_5'$ and $B_6'$ can all be approximated to "L".

The points $B_3'$, $B_4'$, $B_5'$, $B_6'$ correspond to acquisition points (data acquisition points) of the electric field intensity of the electromagnetic wave LT1 at the time of the inspecting target 9 being provisionally arranged such that the optical path 60 is incident orthogonally onto the inspecting target 9. That is, when the inspecting target 9 is arranged along an X-axis line, data of the electric field intensity of the electromagnetic wave LT1 is acquired at an interval of the length L. Hereinafter, this length L may be referred to as "standard data acquisition interval"

As shown in FIG. 8, an intersection point at the time of extending a vertical line from the point $B_3'$ to the line segment $BB_3$ is set as a point $C_3$. Then, a distance b1 between the points B and $B_3$ is expressed by the following equation:

$$b1 = BC_3 + C_3B_3 \quad \text{(Equation 7)}$$
$$= L \cdot \cos\theta + B_3'C_3 \cdot \tan(\theta - \gamma)$$
$$= L \cdot \cos\theta + L \cdot \sin\theta \cdot \tan(\theta - \gamma)$$
$$= L\{\cos\theta + \sin\theta \cdot \tan(\theta - \gamma)\}$$

Further, an intersection point at the time of extending a vertical line from the point $B_4'$ to a line segment $BB_4$ is set as a point $C_4$. Then, a distance b2 between the points $B_3$ and $B_4$ is expressed by the following equation:

$$b2 = BC_4 + C_4B_4 \quad \text{(Equation 8)}$$
$$= L \cdot \cos\theta + B_4'C_4 \cdot \tan(\theta - 2\gamma)$$
$$= 2L \cdot \cos\theta + 2L \cdot \sin\theta \cdot \tan(\theta - 2\gamma)$$
$$= 2L\{\cos\theta + \sin\theta \cdot \tan(\theta - 2\gamma)\}$$

As apparent from Equation 7 and Equation 8, a distance "bn" from the point B (origin) to a data acquisition point (point Bn) at the time of clockwise rotating the galvano mirror 125 by an angle nγ (n is a natural number) is expressed by the following equation:

$$bn = nL\{\cos\theta + \sin\theta \cdot \tan(\theta - n\gamma)\} \quad \text{(Equation 9)}$$

An intersection point at the time of extending a vertical line from the point $B_5'$ to a line segment $BB_5$ is set as a point $C_5$. Then, a distance b1' between the points B and $B_5$ is expressed by the following equation:

$$b1' = BC_5 + C_5B_5 \quad \text{(Equation 10)}$$
$$= L \cdot \cos\theta + B_5'C_5 \cdot \tan(\theta + \gamma)$$
$$= L \cdot \cos\theta + L \cdot \sin\theta \cdot \tan(\theta + \gamma)$$
$$= L\{\cos\theta + \sin\theta \cdot \tan(\theta + \gamma)\}$$

Further, an intersection point at the time of extending a vertical line from the point $B6'$ to a line segment $BB_6$ is set as a point $C_6$. Then, a distance b2' between the points B and $B_6$ is expressed by the following equation:

$$b2' = BC_6 + C_6B_6 \quad \text{(Equation 11)}$$
$$= L \cdot \cos\theta + B_6'C_6 \cdot \tan(\theta + 2\gamma)$$
$$= 2L \cdot \cos\theta + 2L \cdot \sin\theta \cdot \tan(\theta + 2\gamma)$$
$$= 2L\{\cos\theta + \sin\theta \cdot \tan(\theta + 2\gamma)\}$$

As apparent from Equation 10 and Equation 11, a distance "bn'" from the point B to a data acquisition point (point Bn') at the time of counter-clockwise rotating the galvano mirror 125 by an angle nγ (n is a natural number) is expressed by the following equation.

$$bn' = nL\{\cos\theta + \sin\theta \cdot \tan(\theta + n\gamma)\} \quad \text{(Equation 12)}$$

For example, it is assumed that the galvano mirror 125 is clockwise rotated with θ=45°. In this case, from Equation 10, bn≥nL holds when 0°<nγ≤23°. That is, the data acquisition point interval is larger than a standard data acquisition interval L. As opposed to this, when 23°<nγ<90°, the data acquisition point interval is smaller than the standard data acquisition interval L.

As described above, when the electric field intensity data is acquired every time the galvano mirror 125 is rotated at a predetermined angle, the data acquisition interval fluctuates depending on the rotating angle of the galvano mirror 125 (i.e., the incidence angle of the pulsed light LP11). For this reason, when the electric field intensity distribution is imaged with the acquired data taken at regular intervals, a positional distortion occurs as compared with actual electric field intensity distribution. For this reason, it is necessary to correct this positional distortion in order to obtain correct electric field intensity distribution.

For this correction process, a distortion correction factors Xn, Xn' expressed by the following equation are used:

$$Xn = bn/nL = \cos\theta + \sin\theta \cdot \tan(\theta - n\gamma) \quad \text{(Equation 13)}$$

$$Xn' = bn'/nL = \cos\theta + \sin\theta \cdot \tan(\theta + n\gamma) \quad \text{(Equation 14)}$$

Figure 9:
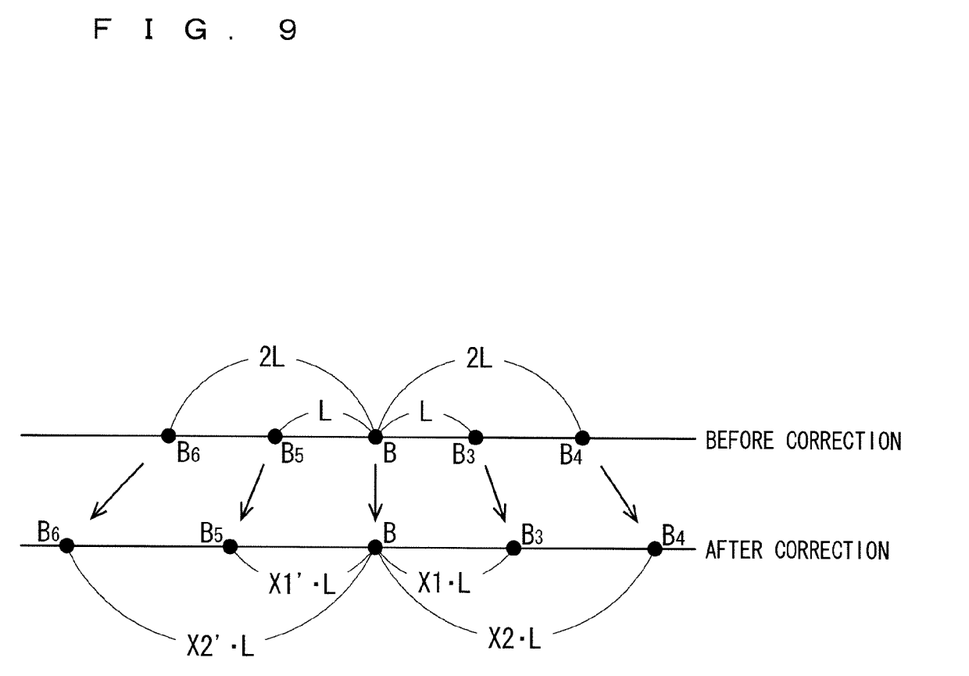
FIG. 9 is a diagram for explaining a state of a correction process.

FIG. 9 is a diagram for explaining a state of the correction process. As shown in FIG. 9, first, the image generation part 21 treats acquired electric field intensity data as data with data acquisition points taken at regular intervals, to generate image data indicating the electric field intensity distribution. In the shown example, data corresponding to the points $B_3$, $B_4$, $B_5$, $B_6$ are arrayed at regular intervals (corresponding to L) to right and left with the point B as an origin, thereby to generate provisional image data of electric field intensity distribution. The position specifying part 211 corrects this image data by use of the distortion correction factors Xn, Xn', to generate image data made to match the actual data acquisition points.

For example, the point $B_3$ is a data acquisition point when n=1. For this reason, the point $B_3$ is corrected such that a distance from the point B is x1 time as long as the distance (corresponding to L) before correction. Similarly, the position specifying part 211 performs positional correction on the other points $B_4$, $B_5$, $B_6$. Specifically, when $\gamma=1.432°$ and $\theta=45°$, $X1=1.38$ and $X2=1.35$ hold from above Equation 13, and $X1'=1.45$, $X2'=1.49$ hold from above Equation 14.

In the present preferred embodiment, by using the correction as described above, it is possible to correct fluctuations in data acquisition interval due to fluctuations in incidence angle at the time of scanning the inspecting target with the pulsed light LP11. Accordingly, it is possible to highly accurately specify a position corresponding to a data acquisition point on an electric field intensity distribution image. Hence it is possible to acquire an image indicating electromagnetic wave intensity distribution suitable for inspection.

It is to be noted that in the above preferred embodiment, the correction is performed after the acquired electromagnetic wave intensity data have been arrayed at regular intervals to generate a provisional image. However, it is considered that the rotating speed of the galvano mirror 125 is controlled such that the data acquisition points are at regular intervals.

Moreover, an object lens, a convex lens or the like may be interposed between the galvano mirror 125 and the inspecting target 9, to narrow the pulsed light LP11. In this case, the above correction process is desirably performed with the narrowed amount taken into consideration.

While the invention has been shown and described in detail, the foregoing description is in all aspects illustrative and not restrictive. It is therefore understood that numerous modifications and variations can be devised without departing from the scope of the invention.

What is claimed is:

1. An inspecting device which takes a semiconductor device or a photo device as an inspecting target, the device comprising:
   a light source for emitting pulsed light;
   a scan part for obliquely irradiating an inspecting target with said pulsed light, while changing an optical path of said pulsed light, to scan said inspecting target with said pulsed light;
   a detection part for detecting an electromagnetic wave emitted non-coaxially with said pulsed light from said inspecting target in accordance with the illumination with said pulsed light; and
   an image generation part for generating an image indicating electric field intensity distribution of said inspecting target based on an electric field intensity of an electromagnetic wave detected by said detection part,
   wherein said image generation part decides a position on said image which corresponds to an acquisition point of an electromagnetic wave intensity based on an incidence angle of said pulsed light on said inspecting target.

2. The inspecting device according to claim 1, wherein
   said detection part is provided with a detector for receiving pulsed light emitted from said light source as probe light, to detect said electromagnetic wave, and
   said inspecting device further includes a delay part for delaying the arrival timing of said probe light at said detector relatively to the arrival timing of said electromagnetic wave.

3. The inspecting device according to claim 1, wherein said image generation part decides said acquisition point of an electromagnetic wave intensity based on fluctuations of data acquisition interval due to fluctuations of said incidence angle.

4. An inspecting method for inspecting a semiconductor device or a photo device as an inspecting target, the method comprising the steps of:
   a) emitting pulsed light from a light source;
   b) obliquely irradiating an inspecting target with said pulsed light emitted in said step (a), while changing an optical path of said pulsed light, to scan said inspecting target with said pulsed light;
   c) detecting an electromagnetic wave emitted non-coaxially with said pulsed light from said inspecting target in accordance with the illumination with said pulsed light in said step (b); and
   (d) generating an image indicating electric field intensity distribution of said inspecting target based on an electric field intensity of an electromagnetic wave detected in said step (c) by an image generation part,
   wherein said image generation part decides a position on said image which corresponds to an acquisition point of an electromagnetic wave intensity based on an incidence angle of said pulsed light on said inspecting target.

5. The inspecting method according to claim 4, wherein said image generation part decides said acquisition point of an electromagnetic wave intensity based on fluctuations of data acquisition interval due to fluctuations of said incidence angle in step (d).

* * * * *